(12) United States Patent
Xie et al.

(10) Patent No.: US 8,304,594 B2
(45) Date of Patent: Nov. 6, 2012

(54) PROCESS FOR INCREASING ETHYLENE AND/OR PROPYLENE YIELD DURING CONVERSION OF OXYGENATES

(75) Inventors: Zaiku Xie, Shanghai (CN); Guozhen Qi, Shanghai (CN); Weimin Yang, Shanghai (CN); Siqing Zhong, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 114 days.

(21) Appl. No.: 12/669,373

(22) PCT Filed: Jul. 17, 2008

(86) PCT No.: PCT/CN2008/001333
§ 371 (c)(1),
(2), (4) Date: Jul. 6, 2010

(87) PCT Pub. No.: WO2009/024012
PCT Pub. Date: Feb. 26, 2009

(65) Prior Publication Data
US 2010/0331596 A1    Dec. 30, 2010

(30) Foreign Application Priority Data
Jul. 18, 2007 (CN) .......................... 2007 1 0043959

(51) Int. Cl.
*C07C 1/00* (2006.01)
(52) U.S. Cl. .................. 585/639; 585/638; 585/640
(58) Field of Classification Search .................. 585/638, 585/639, 640, 641, 642; 422/141, 142
See application file for complete search history.

(56) References Cited

U.S. PATENT DOCUMENTS

| | | | |
|---|---|---|---|
| 4,449,327 A | 5/1984 | Nielsen | |
| 6,166,282 A * | 12/2000 | Miller | 585/638 |
| 6,383,965 B1 * | 5/2002 | Xu | 502/38 |
| 2005/0124838 A1 | 6/2005 | Kuechler et al. | |
| 2006/0025646 A1 | 2/2006 | Fung et al. | |

OTHER PUBLICATIONS

International Search Report and Written Opinion for International Application No. PCT/CN2008/001333 mailed Jan. 1, 2009.

* cited by examiner

*Primary Examiner* — Tam M Nguyen
(74) *Attorney, Agent, or Firm* — Finnegan, Henderson, Farabow, Garrett & Dunner, L.L.P.

(57) ABSTRACT

The present invention provides a process for increasing ethylene and/or propylene yield during conversion of oxygenates using a system comprising a reactor and a regenerator, wherein the reactor comprises a fluidized bed reactor and a riser reactor, which process increases ethylene and/or propylene yield by using a mixture of the deactivated catalyst from the fluidized bed reactor and the regenerated catalyst from the regenerator in the riser reactor for further cracking the $C_4^+$ hydrocarbon stream separated from the product stream.

23 Claims, 2 Drawing Sheets

Figure 1:
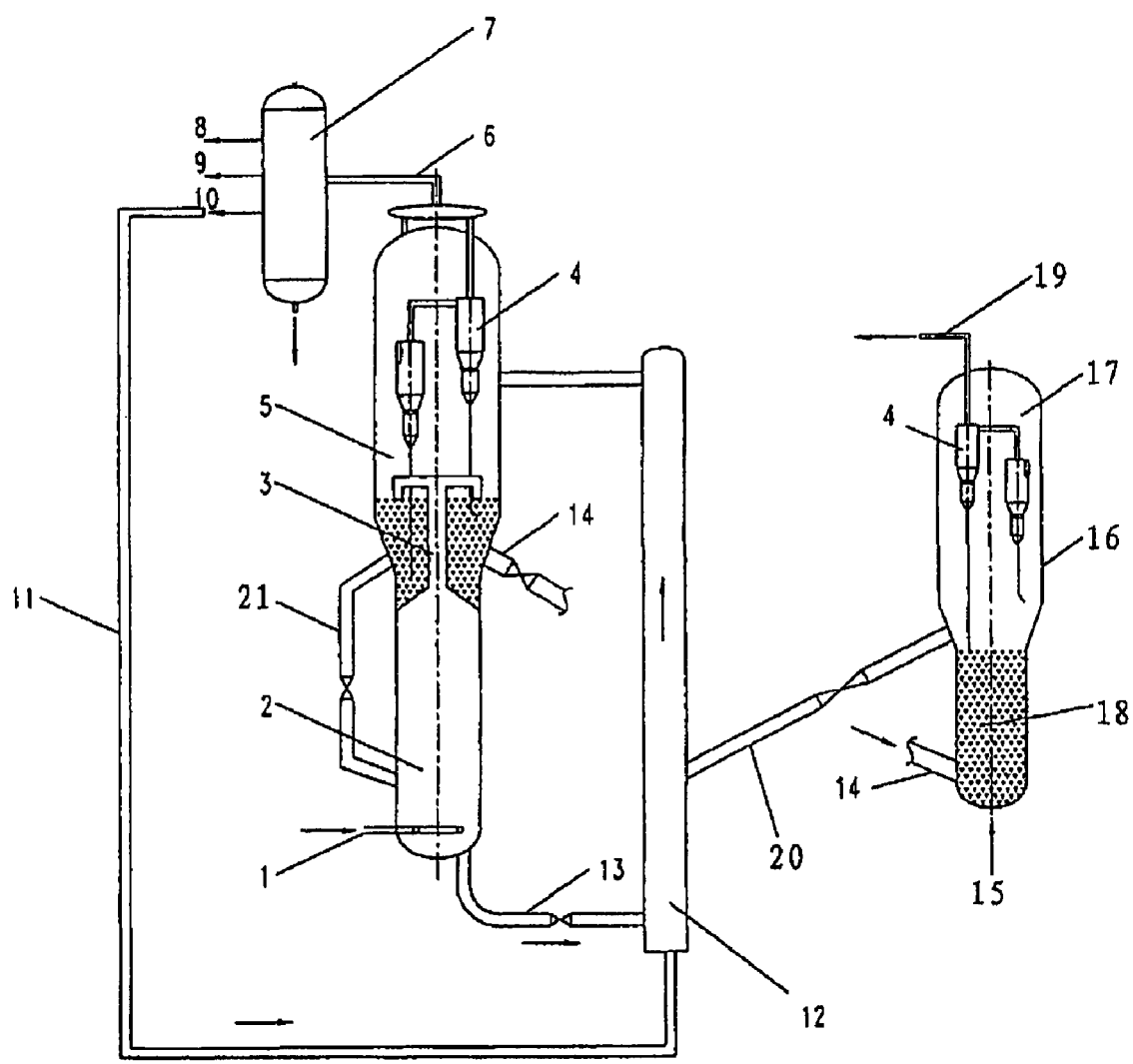

PROCESS FOR INCREASING ETHYLENE AND/OR PROPYLENE YIELD DURING CONVERSION OF OXYGENATES

TECHNICAL FIELD

The present invention relates to a process for increasing ethylene and/or propylene yield during conversion of oxygenates.

BACKGROUND ART

In recent years, more and more attention have been attracted to the process for converting oxygenates such as alcohols (methanol and ethanol), ethers (methyl ether and methyl ethyl ether) and esters (dimethyl carbonate and methyl formate) etc. to olefins (OTO), especially methanol to olefins (MTO).

U.S. Pat. No. 4,499,327 made a detailed study on the use of silicoaluminophosphate molecular sieve catalysts during conversion of oxygenates to light olefins and wherein it is believed that SAPO-34 is the most preferred catalyst for OTO process.

As well known in the art, SAPO-34 catalyst has high selectivity to light olefins and activity. However, in order to ensure high selectivity to light olefins, a required carbon deposition on SAPO-34 catalyst is necessary, therefore, the average carbon deposition on the regenerated catalyst in the regeneration zone has to be controlled at a required level so that the average carbon deposition on the catalyst in the reaction zone can be controlled accordingly. Thus, it is critical for MTO process to control the average carbon deposition on the catalyst in the reaction zone.

US 20060025646 relates to a method for controlling the carbon deposition on the catalyst in the reaction zone during OTO process, wherein a part of the deactivated catalyst is introduced to the regeneration zone to be regenerated by burning out the carbon deposition and the other part of the deactivated catalyst is recycled to the reaction zone for further reaction.

However, the disadvantage of the above-mentioned method is that a big difference is present between the carbon depositions of the deactivated catalyst and the regenerated catalyst entering into the reactor and neither catalyst with more carbon deposition nor catalyst with less carbon deposition is favorable to the selectivity to light olefins, so the light olefin yield would be influenced adversely.

The object of the present invention is further improving the control of the carbon deposition on the catalyst in the reaction zone during OTO process in the prior art, thus further increasing ethylene and/or propylene yield during OTO process.

SUMMARY OF THE INVENTION

With regard to the above-mentioned object, the present invention provides a process for increasing ethylene and/or propylene yield during conversion of oxygenates using a system comprising a reactor and a regenerator, wherein the reactor comprises a fluidized bed reactor and a riser reactor, comprising the following steps:

(a) feeding a feedstock comprising oxygenates to the lower reaction zone of the fluidized bed reactor, wherein the feedstock being converted to a reaction product comprising ethylene, propylene and $C_4^+$ hydrocarbon in the presence of a catalyst, after separated from the catalyst, the reaction product entering into a subsequent separation section to be further separated into a $C_4^+$ hydrocarbon stream, an ethylene product and a propylene product;

(b) feeding the separated $C_4^+$ hydrocarbon stream to the lower reaction zone of the riser reactor, wherein the separated $C_4^+$ hydrocarbon stream being cracked to a reaction product comprising ethylene and propylene in the presence of a catalyst, after passing the upper sedimentation section of the fluidized bed reactor, the reaction product entering into the subsequent separation section, wherein the catalyst in the riser reactor being a mixture of the deactivated catalyst from the fluidized bed reactor and the regenerated catalyst from the regenerator; and (c) the catalyst to be regenerated entering into the regenerator from the fluidized bed reactor after stripped and the regenerated catalyst being recycled to the riser reactor.

According to the process of the present invention, the oxygenate in the feedstock can be selected from the group consisting of methanol, methyl ether and mixture thereof; and the feedstock may further comprise a diluent selected from the group consisting of lower alkanes such as methane, ethane, propane and the like, lower alcohols such as ethanol, n-propanol, iso-propanol, n-butanol, iso-butanol and the like, monocyclic aromatic hydrocarbons, CO, nitrogen and steam, preferably from the group consisting of lower alkanes, lower alcohols and steam, more preferably from the group consisting of lower alcohols and steam, most preferably steam, wherein the volume ratio of the diluent to the feedstock is in range of 0.1:1-10:1, preferably 0.1:1-5:1.

According to the process of the present invention, the regenerator can be in form of a riser, the catalyst is silicoaluminophosphate molecular sieve such as SAPO-11, SAPO-18, SAPO-34, SAPO-56 and the like, preferably SAPO-34, the average carbon deposition on the regenerated catalyst can be adjusted e.g. to a level of less than 6 wt %, preferably less than 3 wt % by varying the superficial gas velocity in the riser regenerator.

According to the process of the present invention, in the reaction zone of the fluidized bed reactor, the superficial gas velocity is in range of 0.6-3 m/s, preferably 0.9-2 m/s, the temperature is in range of 350-600° C., preferably 400-550° C., more preferably 425-500° C., the pressure is in range of 0-1 MPa (gauge), preferably 0.1-0.3 MPa (gauge) and the WHSV of the feedstock is in range of 0.1-20 $hr^{-1}$, preferably 3-8 $hr^{-1}$.

According to the process of the present invention, in the reaction zone of the riser reactor, the temperature is in range of 350-650° C., preferably 450-580° C., the pressure is in range of 0-1 MPa (gauge), preferably 0.1-0.3 MPa (gauge) and the WHSV of the feed is in range of 1-100 $hr^{-1}$, preferably 10-60 $hr^{-1}$.

According to the process of the present invention, in the regenerator, the superficial gas velocity is in range of 3-13 m/s, preferably 5-12 m/s, the temperature is in range of 550-700° C., preferably 600-650° C., and the pressure is in range of 0-1 MPa (gauge), preferably 0.1-0.3 MPa (gauge).

According to the process of the present invention, in the riser reactor the ratio between the mass rates of the deactivated catalyst from the fluidized bed reactor and the regenerated catalyst from the regenerator is in range of 0.2-5, preferably 0.5-2.5; and the regenerated catalyst can be recycled to the riser reactor at multiple axial locations thereof, e.g. at a distance of ¼ and/or ½ of the total height of the riser reactor from bottom thereof.

As well known in the art, during conversion of oxygenates to light olefins, the catalyst with required carbon deposition can improve the selectivity to light olefins, thus increasing the yield of light olefins.

According to the process of the present invention, the regenerated catalyst with less carbon deposition is recycled to the riser reactor firstly and mixed therein with the deactivated catalyst from the fluidized bed reactor at a required ratio between the mass rates thereof such as a ratio of 0.2-5, then in the presence of said mixed catalyst, the $C_4^+$ hydrocarbon stream from the separation section is further cracked to ethylene and/or propylene and a carbon deposition is preformed on the regenerated catalyst. Thus, the average carbon deposition on the catalyst during the whole reaction can be adjusted by varying the above-mentioned ratio between the mass rates and the residence time of the catalyst in the riser reactor to such a level that the yield of light olefins such as ethylene and/or propylene in the product can be increased.

Furthermore, as well known in the art, the conversion of oxygenates to light olefins is highly exothermic, increasing the reaction temperature would result in increased amount of byproducts such as methane, $CO_x$ and the like, thus, the yield of the target product such as ethylene and/or propylene would be decreased; and the cracking reaction of $C_4^+$ hydrocarbon is highly endothermic.

Therefore, according to the process of the present invention, using a part of the deactivated catalyst from the fluidized bed reactor in the riser reactor, not only the average carbon deposition on the catalyst can be adjusted, but also a part of the heat removed from the fluidized bed reactor can be used for cracking $C_4^+$ hydrocarbon, so as to utilize the heat released during conversion of oxygenates to olefins and reduce the temperature in the reaction zone of the fluidized bed reactor to prevent or abate the side reactions such as the pyrolysis of oxygenates effectively.

According to the process of the present invention, during the conversion of methanol and/or methyl ether, the yield of light olefins such as ethylene and/or propylene can be up to 83.37 wt %. Thus, better technical effects can be achieved.

DRAWING DESCRIPTION

Figure 2:
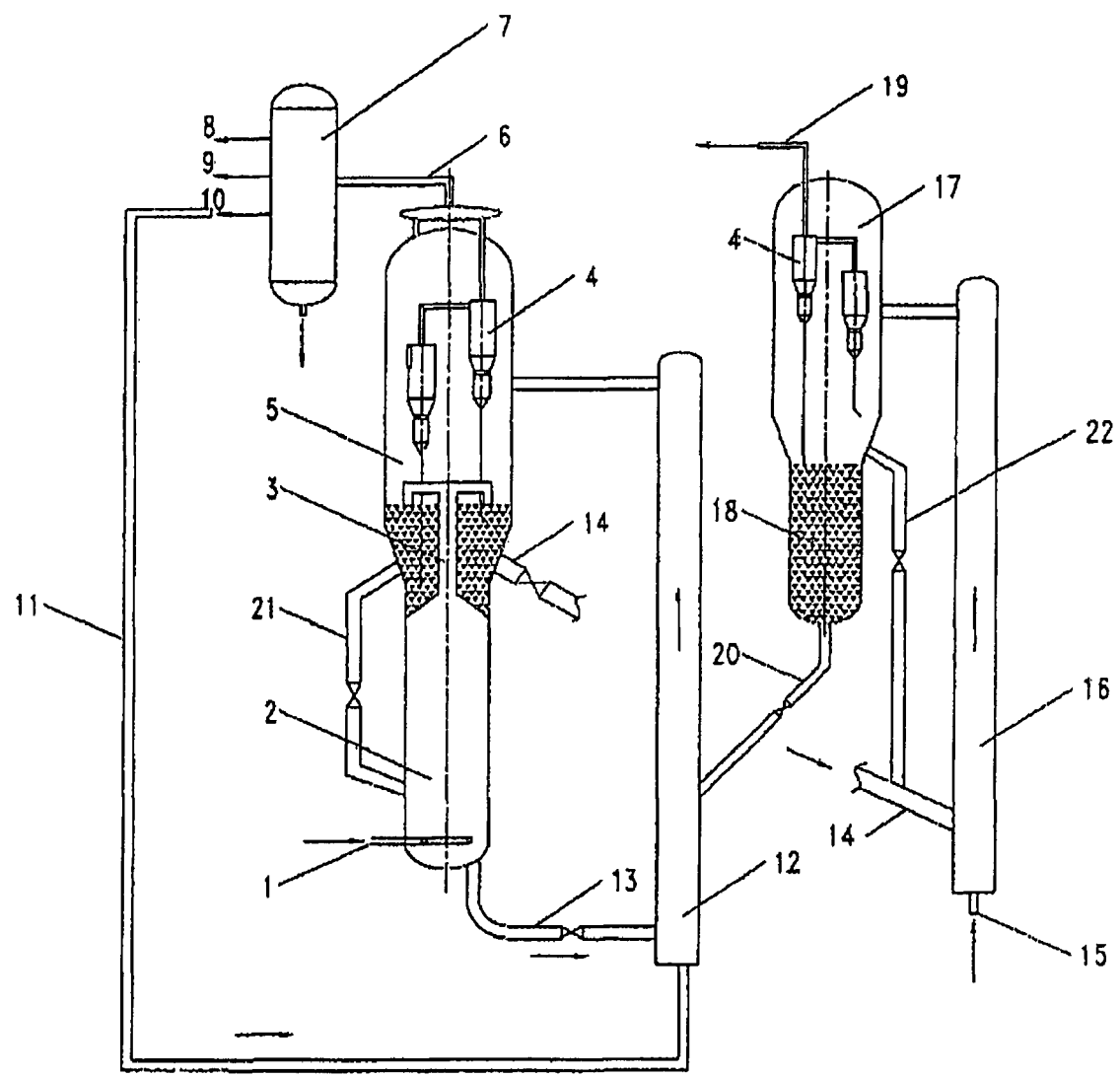

FIG. 1 shows a schematic flow diagram of one embodiment of the process according to the present invention; and FIG. 2 shows a schematic flow diagram of another embodiment of the process according to the present invention.

DETAILED DESCRIPTION OF THE INVENTION

Now the present invention is further described by examples with reference to the accompanying drawings, however, all the examples are not intended to limit the scope of the present invention.

Referring to FIG. 1, the feedstock is entering into the lower reaction zone 2 of the fluidized bed reactor via line 1 and converted therein in the presence of a catalyst, after passing gas-solid fast separation section 3, the reaction product is entering into sedimentation section 5, then through cyclone 4 entering into outlet line 6, therefrom entering into subsequent separation section 7, therein being separated into ethylene product stream 8, propylene product stream 9 and $C_4^+$ hydrocarbon stream 10, wherein the catalyst in sedimentation section 5 can return to reaction zone 2 via line 21 to adjust the catalyst inventory in reaction zone 2; $C_4^+$ hydrocarbon stream 10 is fed into the lower reaction zone of riser reactor 12 via line 11 and cracked therein in the presence of a catalyst, the reaction product is entering into sedimentation section 5 of the fluidized bed reactor and therefrom entering into subsequent separation section 7, wherein the catalyst in riser reactor 12 is a mixture of the deactivated catalyst transported via line 13 from the fluidized bed reactor and the regenerated catalyst transported via line 20 from the regenerator 16; after stripped, the deactivated catalyst in the fluidized bed reactor is introduced into regenerator 16 via line 14 and regenerated therein by burning out carbon deposition in contact with regeneration medium i.e. air, which is fed via line 15, the resultant flue with entrained catalyst is entering into sedimentation section 17 of the regenerator, then through cyclone 4 entering outlet line 19, and the sedimented or separated catalyst is recycled to riser reactor 12 via line 20 from dense phase bed 18.

Referring to FIG. 2, wherein the flow diagram is similar to that in FIG. 1, except for that regenerator 16 being in form of a riser and the regenerated catalyst can return to the lower portion of the riser regenerator from dense phase bed 18 via line 22 to be further regenerated.

EXAMPLE 1-4

In the preferred embodiment of the process according to the present invention as shown in FIG. 2, the fluidized bed reactor is in form of a fast fluidized bed, the regenerator is in form of a riser, the regeneration medium is air, and the regeneration temperature is of 600° C., wherein the average carbon deposition on the regenerated catalyst is adjusted by varying the superficial gas velocity in the riser regenerator; the feedstock to the fluidized bed reactor is pure methanol, and in reaction zone 2 of the fluidized bed reactor, the superficial gas velocity is of 1.2 m/s, the reaction temperature is of 425° C., the reaction pressure is of 0 MPa (gauge), and the WHSV of methanol is of 3 $hr^{-1}$; in riser reactor 12, the feed comprises 80 wt % of $C_4$ hydrocarbon and 20 wt % of $C_5^+$ hydrocarbon, the reaction temperature is of 580° C., the reaction pressure is of 0 MPa (gauge), and the WHSV of the feed is of 60 $hr^{-1}$; the regenerated catalyst is recycled to riser reactor 12 via line 20 at a distance of ¼ of the total height of riser reactor 12 from bottom thereof; in the riser reactor the ratio between the mass rates of the deactivated catalyst from the fluidized bed reactor and the regenerated catalyst from the regenerator is of 0.2; the sampling locations for the regenerated catalyst and the deactivated catalyst are at line 20 and line 14 respectively, and the carbon deposition on the catalyst is analyzed by a high frequency infrared carbon/sulfur detector; the catalyst is a modified SAPO-34 catalyst, which is spray dried and shaped; and the effluent of the fluidized bed reactor is analyzed by an on-line gas chromatography. The experimental data are shown in table 1.

TABLE 1

| Ex. | superficial gas velocity in regenerator, m/s | average carbon deposition on catalyst in reaction zone 2, wt % | carbon deposition on deactivated catalyst, wt % | carbon deposition on regenerated catalyst, wt % | carbon-based ethylene yield, wt % | carbon-based propylene yield, wt % | carbon-based ethylene + propylene yield, wt % |
|---|---|---|---|---|---|---|---|
| 1 | 3.2 | 3 | 8.6 | 1.1 | 37.52 | 43.38 | 80.9 |
| 2 | 5.1 | 5.3 | 8.4 | 2.5 | 38.51 | 43.24 | 81.75 |
| 3 | 6.2 | 5.7 | 8.1 | 3.0 | 39.45 | 42.96 | 82.41 |
| 4 | 12.6 | 6.5 | 7.8 | 5.7 | 39.92 | 41.23 | 81.15 |

EXAMPLE 5-7

Example 2 was repeated except for that the superficial gas velocity in reaction zone 2 of the fluidized bed reactor being of 0.9 m/s, in the riser reactor the ratio between the mass rates of the deactivated catalyst from the fluidized bed reactor and the regenerated catalyst from the regenerator being of 2.5, and the regeneration temperature in the regenerator 16 being varied. The experimental data are shown in table 2.

TABLE 2

| Ex. | regeneration temperature, ° C. | average carbon deposition on catalyst in reaction zone 2, wt % | carbon deposition on regenerated catalyst, wt % | carbon-based ethylene yield, wt % | carbon-based propylene yield, wt % | carbon-based ethylene + propylene yield, wt % |
|---|---|---|---|---|---|---|
| 5 | 550 | 5.8 | 2.8 | 39.28 | 41.31 | 80.59 |
| 6 | 650 | 5.2 | 2.3 | 38.72 | 42.82 | 81.54 |
| 7 | 700 | 4.9 | 1.9 | 37.45 | 43.32 | 80.77 |

EXAMPLE 8-12

Example 3 was repeated except for that the reaction temperature in reaction zone 2 of the fluidized bed reactor being varied. The experimental data are shown in table 3.

TABLE 3

| Ex. | reaction temperature in reaction zone 2, ° C. | carbon deposition on deactivated catalyst, wt % | carbon-based ethylene yield, wt % | carbon-based propylene yield, wt % | carbon-based ethylene + propylene yield, wt % |
|---|---|---|---|---|---|
| 8 | 350 | 7.7 | 34.78 | 44.62 | 79.4 |
| 9 | 400 | 7.9 | 37.21 | 44.23 | 81.44 |
| 10 | 500 | 8.5 | 41.87 | 40.34 | 82.21 |
| 11 | 550 | 8.7 | 42.78 | 37.29 | 80.07 |
| 12 | 600 | 9.1 | 45.32 | 33.62 | 78.94 |

EXAMPLE 13-15

Example 3 was repeated except for that the WHSV of methanol and the superficial gas velocity in reaction zone 2 of the fluidized bed reactor being varied. The experimental data are shown in table 4.

EXAMPLE 16-18

Example 3 was repeated except for that the fluidized bed reactor, the riser reactor and the riser regenerator being operated under same pressure, i.e. the system pressure being common. The experimental data are shown in table 5.

TABLE 4

| Ex. | WHSV of methanol, hr$^{-1}$ | superficial gas velocity in reaction zone 2, m/s | carbon-based ethylene yield, wt % | carbon-based propylene yield, wt % | carbon-based ethylene + propylene yield, wt % |
|---|---|---|---|---|---|
| 13 | 0.12 | 0.6 | 40.45 | 39.96 | 80.41 |
| 14 | 8.11 | 2.0 | 41.88 | 41.49 | 83.37 |
| 15 | 19.45 | 3.0 | 42.57 | 38.26 | 80.83 |

TABLE 5

| Ex. | system pressure, MPa | carbon-based ethylene yield, wt % | carbon-based propylene yield, wt % | carbon-based ethylene + propylene yield, wt % |
|---|---|---|---|---|
| 16 | 0.1 | 37.72 | 42.29 | 80.01 |
| 17 | 0.3 | 36.57 | 41.76 | 78.33 |
| 18 | 1 | 34.76 | 39.58 | 74.34 |

EXAMPLE 19-21

Example 3 was repeated except for that in the riser reactor the ratio between the mass rates of the deactivated catalyst from the fluidized bed reactor and the regenerated catalyst from the regenerator being of 5 and different types of catalysts being used. The experimental data are shown in table 6.

TABLE 6

| Ex. | catalyst | carbon-based ethylene yield, wt % | carbon-based propylene yield, wt % | carbon-based ethylene + propylene yield, wt % |
|---|---|---|---|---|
| 19 | SAPO-11 | 8.13 | 26.89 | 35.02 |
| 20 | SAPO-18 | 38.24 | 41.68 | 78.44 |
| 21 | SAPO-56 | 29.68 | 30.58 | 60.26 |

EXAMPLE 22-23

Example 3 was repeated except for that in the riser reactor the ratio between the mass rates of the deactivated catalyst from the fluidized bed reactor and the regenerated catalyst from the regenerator being of 0.5 and the feedstock to the fluidized bed reactor being varied. The experimental data are shown in table 7.

TABLE 7

| Ex. | feedstock to fluidized bed reactor | volume ratio of methanol to methyl ether | carbon-based ethylene yield, wt % | carbon-based propylene yield, wt % | carbon-based ethylene + propylene yield, wt % |
|---|---|---|---|---|---|
| 22 | methyl ether | ° C. | 39.12 | 43.02 | 82.14 |
| 23 | methanol + methyl ether | 1:0.1 | 39.45 | 42.42 | 81.87 |

EXAMPLE 24-27

Example 3 was repeated except for that in the riser reactor the reaction temperature and the WHSV of the feed being varied. The experimental data are shown in table 8.

TABLE 8

| Ex. | reaction temperature in riser reactor, ° C. | WHSV of feed in riser reactor, hr$^{-1}$ | carbon-based ethylene yield, wt % | carbon-based propylene yield, wt % | carbon-based ethylene + propylene yield, wt % |
|---|---|---|---|---|---|
| 24 | 350 | 1 | 35.79 | 40.35 | 76.14 |
| 25 | 450 | 10 | 36.74 | 40.92 | 77.66 |
| 26 | 580 | 10 | 38.67 | 43.07 | 81.74 |
| 27 | 650 | 100 | 39.06 | 43.14 | 82.20 |

EXAMPLE 28

Example 3 was repeated except for that the regenerated catalyst being recycled to riser reactor 12 via line 20 at a distance of ½ of the total height of riser reactor 12 from bottom thereof. The experimental data are as following: the carbon-based ethylene yield is of 40.62 wt %, the carbon-based propylene yield is of 39.47 wt %, and the carbon-based ethylene+propylene yield is of 80.09 wt %.

EXAMPLE 29-33

Example 3 was repeated except for that the reaction temperature in reaction zone 2 of the fluidized bed reactor being of 475° C. and the feedstock to the fluidized bed reactor further comprising a diluent. The experimental data are shown in table 9.

TABLE 9

| Ex. | diluent | mass ratio of diluent to methanol | carbon-based ethylene yield, wt % | carbon-based propylene yield, wt % | carbon-based ethylene + propylene yield, wt % |
|---|---|---|---|---|---|
| 29 | methane | 5:1 | 39.45 | 39.61 | 79.06 |
| 30 | CO | 0.1:1 | 40.23 | 39.87 | 80.10 |

TABLE 9-continued

| Ex. | diluent | mass ratio of diluent to methanol | carbon-based ethylene yield, wt % | carbon-based propylene yield, wt % | carbon-based ethylene + propylene yield, wt % |
|---|---|---|---|---|---|
| 31 | steam | 0.1:1 | 42.94 | 39.83 | 82.77 |
| 32 | ethanol | 10:1 | 60.67 | 18.86 | 79.53 |
| 33 | benzene | 0.1:1 | 39.42 | 39.48 | 79.90 |

EXAMPLE 34

Example 1 was repeated except for that the regenerator being in form of a fluidized bed. The experimental data are as following: the carbon-based ethylene yield is of 38.61 wt %, the carbon-based propylene yield is of 39.19 wt %, and the carbon-based ethylene+propylene yield is of 77.80 wt %.

COMPARATIVE EXAMPLE 1

The fluidized bed reactor is in form of a fast fluidized bed, the riser reactor is eliminated, the regenerator is in form of a fluidized bed, the regeneration medium is air, and the regeneration temperature is of 600° C.; the feedstock to the fluidized bed reactor is pure methanol, and in reaction zone 2 of the fluidized bed reactor, the superficial gas velocity is of 1.2 m/s, the reaction temperature is of 425° C., the reaction pressure is of 0 MPa (gauge), and the WHSV of methanol is of 3 hr$^{-1}$; the catalyst is a modified SAPO-34 catalyst, which is spray dried and shaped; the regenerated catalyst is recycled into reaction zone 2 and has a carbon deposition of 0.08 wt %, and the average carbon deposition on the mixed catalyst in reaction zone 2 is of 2.8 wt %, the carbon deposition on the catalyst is analyzed by a high frequency infrared carbon/sulfur detector; and the effluent of the fluidized bed reactor is analyzed by an on-line gas chromatography. The experimental data are as following: the carbon-based ethylene yield is of 37.33 wt %, the carbon-based propylene yield is of 38.81 wt %, and the carbon-based ethylene+propylene yield is of 76.14 wt %.

COMPARATIVE EXAMPLE 2

Comparative example 1 was repeated except for that the reaction temperature in reaction zone 2 being of 500° C., $C_4$ hydrocarbon being sprayed through nozzles along the axis of the reaction zone at a distance of ¼ of the total height of reaction zone 2 from the distribution plate at bottom thereof, wherein the mass ratio of $C_4$ hydrocarbon to methanol being of 1:8. The experimental data are as following: the carbon-based ethylene yield is of 38.09 wt %, the carbon-based propylene yield is of 40.17 wt %, and the carbon-based ethylene+propylene yield is of 78.26 wt %.

As can be known from the experimental data, all the examples have effected the present invention using different feedstocks and different catalysts under various process conditions respectively and obtained higher ethylene and/or propylene yield compared with the comparative examples. Therefore, the process according to the present invention can increase the ethylene and/or propylene yield during conversion of oxygenates significantly.

The invention claimed is:

1. A process for increasing ethylene and/or propylene yield during conversion of oxygenates using a system comprising a reactor and a regenerator, wherein the reactor comprises a fluidized bed reactor and a riser reactor, comprising:
 (a) feeding a feedstock comprising an oxygenate to the lower reaction zone of the fluidized bed reactor, wherein the feedstock being converted to a reaction product comprising ethylene, propylene and $C_4^+$ hydrocarbon in the presence of a catalyst, after separated from the catalyst, the reaction product entering into a subsequent separation section to be further separated into a $C_4^+$ hydrocarbon stream, an ethylene product and a propylene product;
 (b) feeding the separated $C_4^+$ hydrocarbon stream to the lower reaction zone of the riser reactor, wherein the separated $C_4^+$ hydrocarbon stream being cracked to a reaction product comprising ethylene and propylene in the presence of a catalyst, after passing the upper sedimentation section of the fluidized bed reactor, the reaction product entering into the subsequent separation section, wherein the catalyst in the riser reactor being a mixture of the deactivated catalyst from the fluidized bed reactor and the regenerated catalyst from the regenerator with a ratio between their mass rates in the range of 0.2-5; and
 (c) the catalyst to be regenerated entering into the regenerator from the fluidized bed reactor after stripped, and the regenerated catalyst having an average carbon deposition of less than 6 wt % relative to its total weight and being recycled to the riser reactor.

2. The process according to claim 1, wherein the oxygenate is selected from methanol, methyl ether and mixture thereof.

3. The process according to claim 1, wherein the feedstock further comprises a diluent selected from lower alkanes, lower alcohols, monocyclic aromatic hydrocarbons, CO, nitrogen and steam, wherein the volume ratio of the diluent to the feedstock is in the range of 0.1:1-10:1.

4. The process according to claim 3, wherein the diluent is selected from steam.

5. The process according to claim 3, wherein the volume ratio of the diluent to the feedstock is in the range of 0.1:1-5:1.

6. The process according to claim 1, wherein the regenerator is in the form of a riser.

7. The process according to claim 1, wherein in the reaction zone of the fluidized bed reactor, the superficial gas velocity is in the range of 0.6-3 m/s, the temperature is in the range of 350-600° C., the pressure is in the range of 0-1 MPa (gauge), and the WHSV of the feedstock is in the range of 0.1-20 hr$^{-1}$.

8. The process according to claim 7, wherein the superficial gas velocity is in the range of 0.9-2 m/s.

9. The process according to claim 7, wherein the temperature is in the range of 425-500° C.

10. The process according to claim 7, wherein the pressure is in the range of 0.1-0.3 MPa (gauge).

11. The process according to claim 7, wherein the WHSV of the feedstock is in the range of 3-8 hr$^{-1}$.

12. The process according to claim 1, wherein in the reaction zone of the riser reactor, the temperature is in the range of 350-650° C., the pressure is in the range of 0-1 MPa (gauge), and the WHSV of the feed is in the range of 1-100 hr$^{-1}$.

13. The process according to claim 12, wherein the temperature is in the range of 450-580° C.

14. The process according to claim 12, wherein the pressure is in the range of 0.1-0.3 MPa (gauge).

15. The process according to claim 12, wherein the WHSV of the feed is in the range of 10-60 $hr^{-1}$.

16. The process according to claim 1, wherein in the regenerator, the superficial gas velocity is in the range of 3-13 m/s, the temperature is in the range of 550-700° C., and the pressure is in the range of 0-1 MPa (gauge).

17. The process according to claim 16, wherein the superficial gas velocity is in the range of 5-12 m/s.

18. The process according to claim 16, wherein the temperature is in the range of 600-650° C.

19. The process according to claim 18, wherein the pressure is in the range of 0.1-0.3 MPa (gauge).

20. The process according to claim 1, wherein the catalyst is SAPO 34.

21. The process according to claim 1, wherein the regenerated catalyst has an average carbon deposition of less than 3 wt % relative to total weight of the regenerated catalyst.

22. The process according to claim 1, wherein in the riser reactor the ratio between the mass rates of the deactivated catalyst from the fluidized bed reactor and the regenerated catalyst from the regenerator is in the range of 0.5-2.5.

23. The process according to claim 1, wherein the regenerated catalyst is recycled to the riser reactor at multiple axial locations thereof.

* * * * *